United States Patent
Krueger et al.

(10) Patent No.: US 10,610,665 B2
(45) Date of Patent: Apr. 7, 2020

(54) BODY CAVITY DRAINAGE CATHETER WITH MICROTEXTURED SURFACE

(71) Applicant: CareFusion 2200, Inc., San Diego, CA (US)

(72) Inventors: John Krueger, Muskego, WI (US); Maya Prakash Singh, Bardonia, NY (US); Thomas Wilschke, Chicago, IL (US)

(73) Assignee: CareFusion 2200, Inc., San Diego, CA (US)

( * ) Notice: Subject to any disclaimer, the term of this patent is extended or adjusted under 35 U.S.C. 154(b) by 285 days.

(21) Appl. No.: 15/169,410

(22) Filed: May 31, 2016

(65) Prior Publication Data

US 2017/0340859 A1    Nov. 30, 2017

(51) Int. Cl.
- A61M 25/00 (2006.01)
- A61M 1/28 (2006.01)
- A61M 27/00 (2006.01)

(52) U.S. Cl.
CPC ........ *A61M 25/0043* (2013.01); *A61M 1/285* (2013.01); *A61M 25/007* (2013.01); *A61M 27/00* (2013.01); *A61M 2025/006* (2013.01); *A61M 2025/0056* (2013.01); *A61M 2210/101* (2013.01); *A61M 2210/1017* (2013.01)

(58) Field of Classification Search
CPC .......... A61M 1/285; A61M 2025/0056; A61M 2025/006; A61M 2210/101; A61M 2210/1017; A61M 25/0043; A61M 25/007; A61M 27/00
See application file for complete search history.

(56) References Cited

U.S. PATENT DOCUMENTS

| | | | | |
|---|---|---|---|---|
| 5,019,096 A | * | 5/1991 | Fox, Jr. | A61B 42/10 2/167 |
| 5,484,401 A | * | 1/1996 | Rodriguez | A61M 1/008 604/28 |
| 2016/0038650 A1 | * | 2/2016 | Griffith | A61L 29/16 604/265 |

FOREIGN PATENT DOCUMENTS

WO    WO2013003373 A1    1/2013

OTHER PUBLICATIONS

First Office Action for China Patent Application No. 201720596992.8 dated Jun. 12, 208 (with English translation) (6 pp.).
Office Action dated Aug. 28, 2019 pertaining to Chinese Patent Application No. 2017103822552.

* cited by examiner

*Primary Examiner* — Kai H Weng
(74) *Attorney, Agent, or Firm* — Dinsmore & Shohl LLP (57) ABSTRACT

A catheter configured for partial implantation into a patient and drainage of a body cavity may be provided with microtextured surface on one or more inner diameter surfaces and/or outer diameter surfaces of the tubular catheter body. The microtexturing may include surface features dimensioned to inhibit colonization and/or migration of microbes. The microtexturing may also include channels or other recesses containing an antimicrobial agent such as chlorhexidine gluconate or any other effective antimicrobial agent.

14 Claims, 7 Drawing Sheets

BODY CAVITY DRAINAGE CATHETER WITH MICROTEXTURED SURFACE

TECHNICAL FIELD

Embodiments disclosed herein generally relate to a medical patient body cavity drainage catheter. More particularly, the disclosed embodiments relate to such a drainage catheter (e.g., for effusions and/or ascites) with one or more microtextured surfaces.

BACKGROUND

Figure 1A:
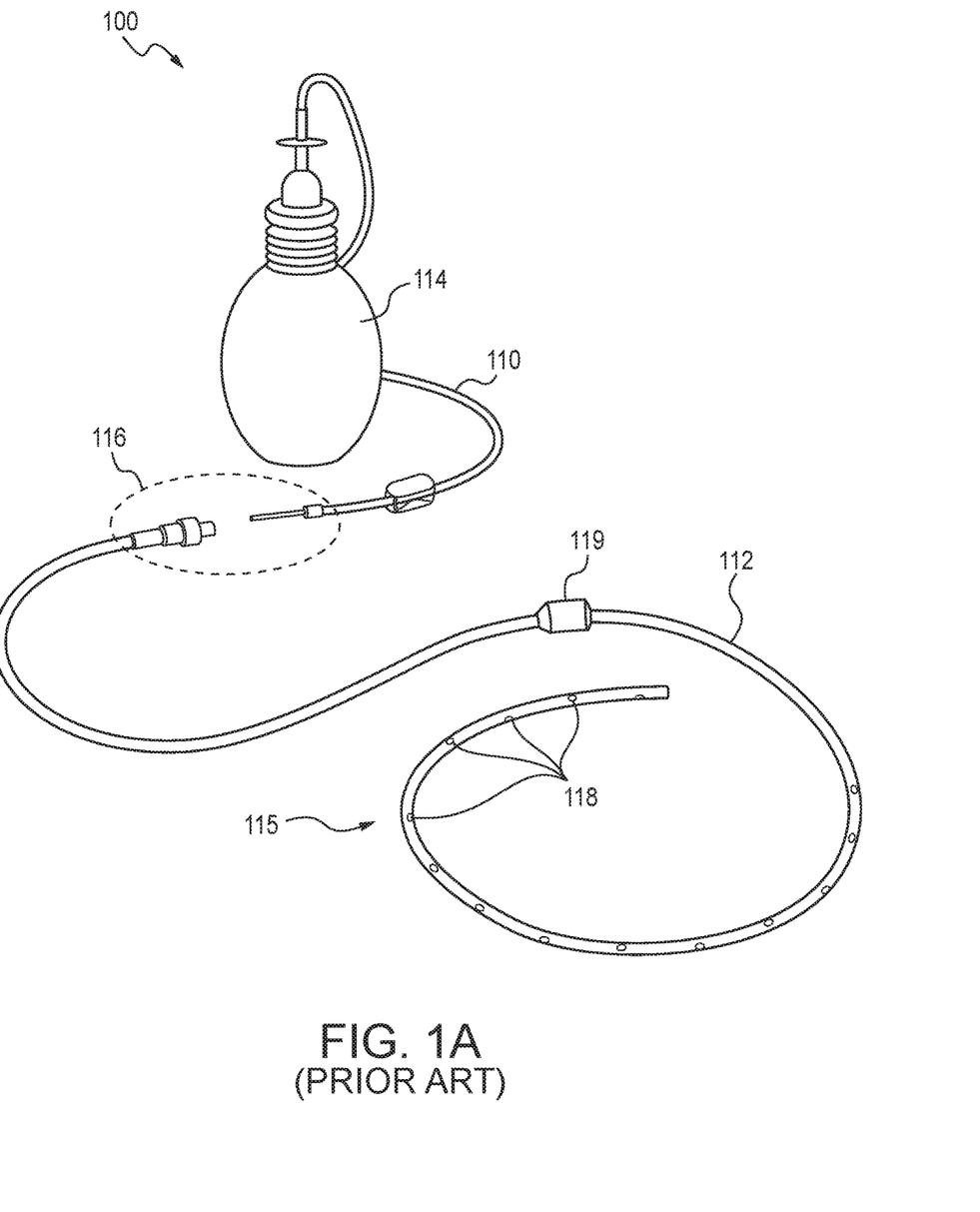
FIG. 1A shows an exemplary body cavity drainage catheter system including a vacuum bottle.
Figure 1B:
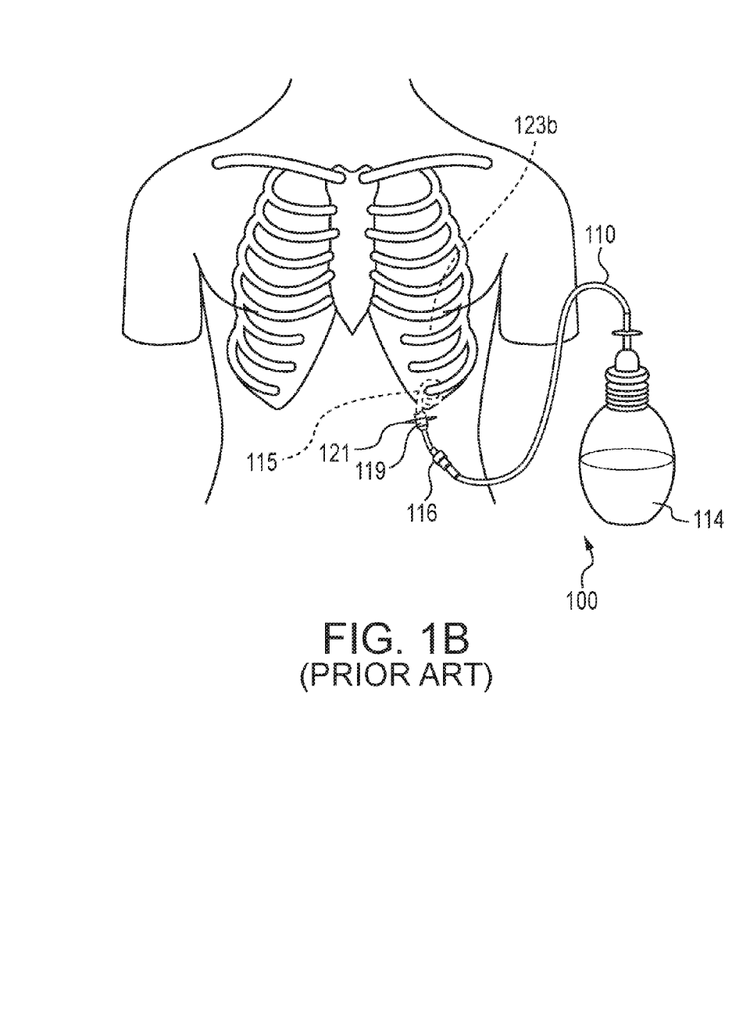
FIGS. 1B-1C show, respectively, the system of FIG. 1A implemented for pleural drainage and peritoneal drainage.
Figure 1C:
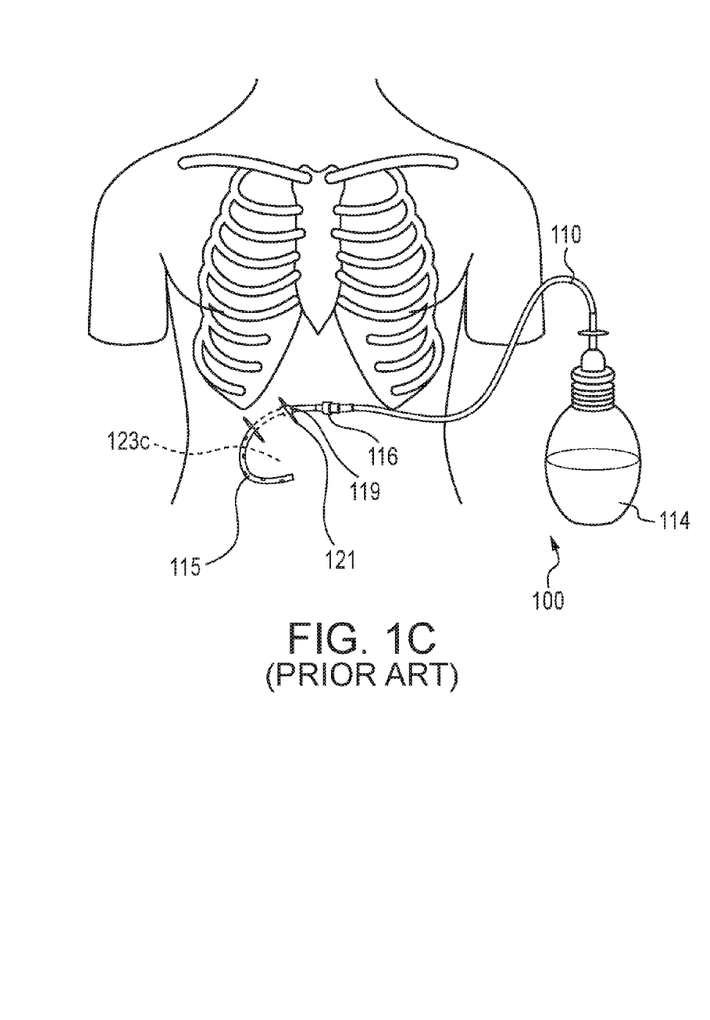

Ascites describes an accumulation of fluid and other materials in the peritoneal or other body cavity. Pleural effusion refers to the effusion of fluid into the pleural space. Both excess fluid accumulation conditions may be treated with a drainage apparatus 100 of the type shown partially disassembled in FIG. 1A. The apparatus 100 is shown in FIGS. 1B-1C as assembled and installed in a patient body (respectively, for pleural and peritoneal drainage) and includes a drainage container 114, typically a vacuum bottle. The drainage container 114 is removably attached by a proximal tube 110 at a two-piece, one-way valve 116 to a body-contacting distal catheter 112. The valve 116 may be configured in any number of ways known in the art for attaching catheters together in a fluid-patent manner, (which may include a two-part valve), and the proximal portion attached to the distal catheter 112 may be configured to be self-sealing when disconnected from the proximal tube 110. The distal end portion of the distal catheter 112 is shown indwelling the patient, disposed through the body wall 121 into an intra-body space 123b/123c, which may be—for example—a pleural cavity/space (e.g., FIG. 1B), peritoneal cavity/space (e.g., FIG. 1C), or other body cavity. That distal portion includes a sealing cuff 119 and a flexible fluid-intake length 115 including fenestrations 118 which—when the device is used—are located in the intra-body spaces 123b/123c. This structure may be better understood with reference to U.S. Pat. No. 5,484,401, which is incorporated herein by reference, and with reference to commercial products marketed under the name PleurX® by CareFusion® of San Diego, Calif. (a Becton Dickinson Company).

The pleural space (the thin, fluid-filled space between the two pulmonary pleurae—visceral and parietal—of each lung) of a healthy person normally contains approximately 5 to 20 ml of fluid due to a physiologically-maintained balance between rates of secretion and resorption of pleural fluid. The pH, glucose and electrolytes of the fluid are equilibrated with plasma, but the fluid is relatively protein-free. The fluid is the result of the hydrostatic-oncotic pressure of the capillaries of the parietal pleura. About 80-90% of the fluid is reabsorbed by the pulmonary venous capillaries of the visceral pleura, and the remaining 10-20% is reabsorbed by the pleural lymphatic system. The turnover of fluid in the pleural space is normally quite rapid—roughly 35 to 75% of the total fluid per hour, so that 5 to 10 liters of fluid move through the pleural space each day.

A disruption in the balance between the movement of fluid into the pleural space and the movement of fluid out of the pleural space may produce excessive fluid accumulation in the pleural space. Such disruptions may include, for example, (1) increased capillary permeability resulting from inflammatory processes such as pneumonia, (2) increased hydrostatic pressure as in congestive heart failure, (3) increased negative intrapleural pressure as seen in atelectasis (partial or total lung collapse), (4) decreased oncotic pressure as occurs in the nephrotic syndrome with hypoalbuminemia, and (5) increased oncotic pressure of pleural fluid as occurs in the inflammation of pleural tumor growth or infection. Pleural effusion is particularly common in patients with disseminated breast cancer, lung cancer or lymphatic cancer and patients with congestive heart failure, but also occurs in patients with nearly all other forms of malignancy.

The clinical manifestations of pleural effusion include dyspnea, cough and chest pain which diminish the patient's quality of life. Although pleural effusion typically occurs toward the end of terminal malignancies such as breast cancer, it occurs earlier in other diseases. Therefore relieving the clinical manifestations of pleural effusion is of a real and extended advantage to the patient. For example, non-breast cancer patients with pleural effusion have been known to survive for years.

There are a number of treatments for pleural effusion. If the patient is asymptomatic and the effusion is known to be malignant or paramalignant, treatment may not be required. Such patients may develop progressive pleural effusions that eventually do produce symptoms requiring treatment, but some will reach a stage where the effusions and reabsorption reach an equilibrium that is still asymptomatic and does not necessitate treatment.

Pleurectomy and pleural abrasion is generally effective in obliterating the pleural space and, thus, controlling the malignant pleural effusion. This procedure is done in many patients who undergo thoracotomy for an undiagnosed pleural effusion and are found to have malignancy, since this would prevent the subsequent development of a symptomatic pleural effusion. However, pleurectomy is a major surgical procedure associated with substantial morbidity and some mortality. Therefore, this procedure is usually reserved for patients with an expected survival of at least several months, who are in relative good condition, who have a trapped lung, or who have failed a sclerosing agent procedure.

In general, systemic chemotherapy is disappointing for the control of malignant pleural effusions. However, patients with lymphoma, breast cancer, or small cell carcinoma of the lung may obtain an excellent response to chemotherapy. Another approach to removing fluid from the pleural space has been to surgically implant a chest tube. Such tubes are commonly quite rigid and fairly large in diameter and are implanted by making a surgical incision and spreading apart adjacent ribs to fit the tube into place. Such procedures are painful to the patient, both initially when the chest tube is inserted and during the time it remains within the pleural space.

Thoracentesis is a common approach to removing pleural fluid, in which a needled catheter is introduced into the pleural space through an incision in the chest cavity and fluid is positively drawn out through the catheter using a syringe or a vacuum source. The procedure may also include aspiration utilizing a separate syringe. There are a number of difficulties in thoracentesis, including the risk of puncturing a lung with the catheter tip or with the needle used to introduce the catheter, the risk of collapsing a lung by relieving the negative pressure in the pleural space, the possibility of aggravating the pleural effusion by stimulating fluid production in the introduction of the catheter, and the risk of infection. One of the primary difficulties with ordinary thoracentesis procedures is that fluid reaccumulates in the pleural space relatively quickly after the procedure is performed, and so it is necessary to perform the procedure repeatedly—as often as every few days. Similar techniques and difficulties exist for certain abdominal/peritoneal conditions. The drainage procedures using this type of device can be done by a patient or other non-medical-professional caregiver (e.g., in the home or elsewhere), and—with proper simple training and technique—infection risk is low. However, it would still be advantageous to provide improved methods for treating pleural effusions, peritoneal ascites, and other conditions, including providing construction features that may inhibit microbial growth on the drainage catheter—particularly in locations that such microbes could enter the patient, and/or that may provide for and/or enhance sealing growth of patient tissue to and around the drainage catheter.

BRIEF SUMMARY

In one aspect, embodiments disclosed herein may include a body cavity drainage catheter, which includes an elongate tubular body including a longitudinal lumen defined by a catheter wall; a first lengthwise portion of the tubular body configured for indwelling a patient body; a second lengthwise portion of the tubular body configured for disposition outside a patient body and further including a valve at a terminal end of the tubular body; and which may also include a cuff element defining a border between the first lengthwise portion and the second lengthwise portion, said cuff configured for ingrowth by patient tissue in a manner forming an effective seal around an outer diameter of the tubular body; and at least one lengthwise region of the second lengthwise portion including a microtextured surface disposed along an inner diameter surface, an outer diameter surface, or both. The embodiments may include microtextured surfaces on other regions and/or antimicrobial compounds, as well as methods for making and using device embodiments described herein.

DETAILED DESCRIPTION

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

Embodiments here may use the illustrated examples of microtextured (regularly patterned, irregularly patterned, or unpatterned) surfaces. They may include or exclude surface treatments and/or embedded/elutable antimicrobial compounds that may enhance the microbe colonization-inhibitory function of the described embodiments' physical topography. For embodiments configured (with or without a cuff) with microtexturing that promotes sealing growth of patient tissue around the catheter's outer circumference, it may be useful to include one or more growth factors or other compounds (with or without the presence of antimicrobial compounds), so as to enhance the efficacy of this structure and function while also providing for the other functions described herein. Embodiments also include treating a device described, which initially lacks an antimicrobial agent, with a surface washing and/or other antimicrobial surface treatment that preferably will leave some at least one antimicrobial agent on the microtextured surface—preferably within recessed surfaces thereof. Microtextured surfaces may be included on internal and/or external surfaces of a tubular drainage catheter body over its entirety, or may be on less than an entire surface—for example—in region(s) immediately adjacent its cuff, and/or in region(s) immediately adjacent its valve, where the microtextured surface regions in certain embodiments are surfaces that do not contact an internal portion of a patient's body. In other embodiments, a microtextured surface may be configured to encourage adhesive growth of the epidermis of a patient, where such a surface may be provided on an external catheter surface under (or even instead of) the cuff, thereby forming the seal around the tubular catheter body between its outer circumference and the patient's body wall.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. Reference herein to any industry standards (e.g., ASTM, ANSI, IEEE standards) is defined as complying with the currently published standards as of the original filing date of this disclosure concerning the units, measurements, and testing criteria communicated by those standards unless expressly otherwise defined herein.

The terms "proximal" and "distal" are used from the perspective of a person (e.g., doctor or other caregiver) treating or otherwise interacting with a patient and refer, respectively, to a handle/doctor-end of a device or related object and a tool/patient-end of a device or related object. The terms "about," "substantially," "generally," and other terms of degree, when used with reference to any volume, dimension, proportion, or other quantitative value, are intended to communicate a definite and identifiable value within the standard parameters that would be understood by one of skill in the art (equivalent to a medical device engineer with experience in this field), and should be interpreted to include at least any legal equivalents, minor but functionally-insignificant variants, standard manufacturing tolerances, and including at least mathematically significant figures (although not required to be as broad as the largest range thereof). The term "microtextured" refers to a surface where at least one dimension of each surface feature of a plurality of upstanding and/or recessed surface features has a height, length or width that is less than 50 µm, where in certain embodiments at least two of those surface dimensions are less than 50 µm.

Figures 2, 2A:
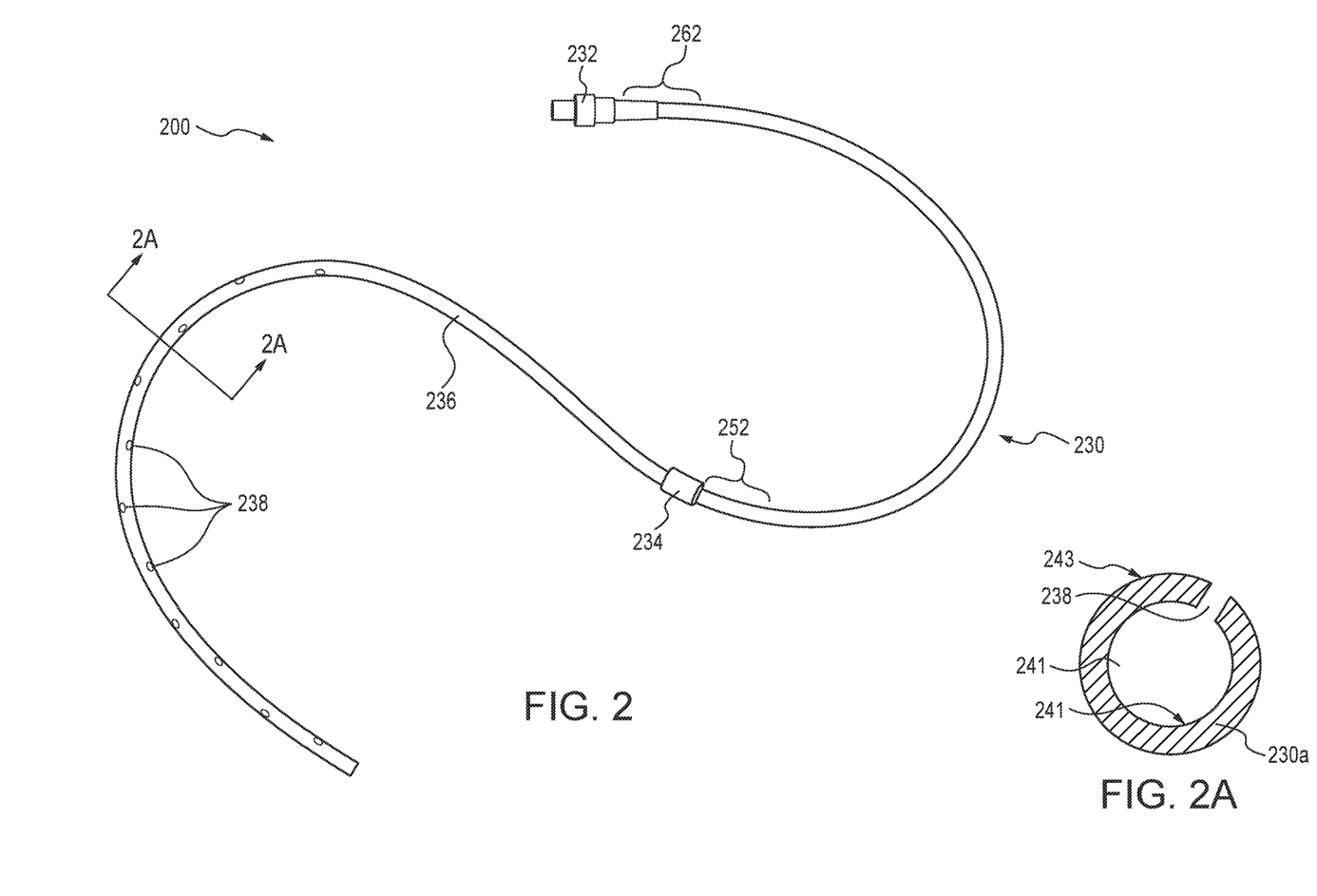
FIG. 2 depicts a drainage tube assembly, with locations identified for implementation of the present inventive disclosure.
FIG. 2A shows a transverse section view taken along line 2A-2A of FIG. 2.

Embodiments of a body cavity drainage catheter 200 are described with reference to FIG. 2. Preferred embodiments will include microtexturing on surfaces of the catheter device 200 that may be more susceptible to bacterial colonization that could gain access to a patient's body via the catheter. The illustrated body cavity drainage catheter 200 includes a tubular body 230 that may be a unitary construction seamless from end to end, or that may be constructed of conjoined tubular segments. The proximal end includes a one-way valve 232 configured for sealing, one-way-flow connection with a mating valve of a drainage device (e.g., a vacuum drainage bottle such as shown in FIG. 1A, another vacuum bottle, another vacuum source, or another drainage implement).

Midway along the tubular body 230, a Dacron™ cuff 234 is shown encircling/encompassing the outer circumference. This cuff 234 may be made of different materials than Dacron™, and it is configured to contact the patient's skin at the location where the catheter enters the patient's body (see, e.g., FIGS. 1B-1C). The cuff 234 preferably is configured to contact the surfaces of an incision through the patient's skin (e.g., as shown at the external body wall 121 in FIGS. 1B-1C) and to be ingrown there by the patient's skin in order to form a sealed barrier continuous and contiguous with the rest of the patient's skin as an integrated part of his/her natural epidermal barrier. A closed/patent tube length (defining an internal longitudinal tube lumen) extends from the valve 232 through the cuff 234. In the present description, as a matter of convenient reference, the device length from the cuff toward and including the valve is referred to as the proximal portion, and the length opposite the cuff is referred to as the distal portion, so that the valve 232 defines a proximal device end, and the opposite terminal tube end defines a distal device end with an intermediate tube length therebetween.

The closed/patent tube length extends distally past the cuff to a fenestrated distal tube length 236, which includes a plurality of fenestrations/apertures 238 that provide fluid communication across the wall defining the tube construction into the tube lumen. FIG. 2A shows a transverse section view taken along line 2A-2A of FIG. 2, showing the tube lumen 231, an aperture 238 open thereto, the solid construction of the tube wall 230a, the tube's inner diameter surface 241, and the tube's outer diameter surface 243. For the presently disclosed embodiments, at least those areas that may be at greater risk of microbe colonization (e.g., bacterial, fungal, or other) preferably will include microtextured surface.

With respect to the tube body 230, the entire inner diameter surface, the entire outer diameter surface, or both may be microtextured. However, there may not be a need to provide that extensive of microtextured surface areas. As such, the microtexturing may be limited to any lengthwise region along one or both of the inner diameter surface, and the outer diameter surface. For example, at least a lengthwise portion 252 of the outer diameter surface immediately adjacent and proximal of the cuff 234 may include microtextured surface—where it is most preferable for any such microtextured surface region to extend around the entire circumference of a longitudinal surface region. This microtextured lengthwise portion may extend up to about 3 inches (about 7.6 cm) in some embodiments, and the same or a different lengthwise portion distal of the cuff may include microtextured surface, also or instead, and may extend up to an entire length. For this device, the cuff 234 forms an effective continuous barrier when ingrown with the patient's epidermis. Providing the microtextured surface on that immediately adjacent lengthwise region (which may extend along the outer diameter surface covered by the cuff) may inhibit microbial colonization and migration in/toward the patient's body—particularly until the cuff is ingrown and the patient's natural epidermal barrier is effectively closed again after the tube-insertion incision has healed into and around the cuff. The microtextured lengthwise portion preferably will be at least 0.5 cm, and may extend 2 cm or more, and may encompass an entire surface area.

In that embodiment or another embodiment, a proximal-end region of the device 200 may include microtextured surface. Specifically, a proximal tube length 262 immediately adjacent (and optionally encompassing) at least a portion of the valve 232 may include microtextured surface on at least the outer diameter surface. Although the valve may generally be effective to prevent microbial invasion—particularly in view of the fact that the device is used under a vacuum that pulls out away from the patient—the inner diameter surface may also include microtextured surface. In such embodiments, the microtextured inner diameter surface will reduce the ability of organisms to attach, colonize, and/or migrate, where provision of vacuum forces may further help break up and flush out any organism(s) that may attempt to attach and grow in the area near the valve. As noted above, the microtextured surface preferably will cover the entire circumference along a lengthwise portion of the tubular body. The reason for this will be apparent with reference to the microtextured surface description below—as a lengthwise interruption in that would disrupt its intended efficacy as a barrier (e.g., providing a "bridge" for microbial colonization and migration).

In preferred embodiments, the microtextured surface of a drainage catheter will include particular surface textures (either internally or externally or both) that may prevent undesired bacterial contamination of such surfaces, and specifically that are configured to inhibit and/or minimize bacterial colonization and migration. One particular aspect of various embodiments may include a microtextured surface commercially generally known as Sharklet™. Sharklet™ is a proprietary technology configured to inhibit bacterial survival, growth, transfer and migration through surface patterning alone. The Sharklet™ surface is comprised of millions of tiny diamonds arranged in a distinct pattern that mimics the microbe-resistant properties of shark skin.

Technologies used in the Sharklet™ commercial products are described in U.S. Pat. No. 9,045,651 to Chen et al.; U.S. Pat. No. 9,016,221 to Brennan et al.; U.S. Pat. No. 8,997,672 to Brennan et al.; U.S. Pat. No. 7,650,848 to Brennan et al.; U.S. Pat. No. 7,347,970 to Kim et al.; U.S. Pat. No. 7,143,709 to Brennan et al.; and U.S. Pat. No. 7,117,807 to Bohn, Jr. et al., the disclosures for each of which are incorporated by reference herein in their entirety. Sharklet™ is also described in U.S. Patent Publication Nos. 2010/0126404 to Brennan et al., and 2010/0119755 to Chung et al. and PCT Pat. App. Publ. No. WO 2011/071892 to Magin, et al., the entire disclosures for each of which are incorporated by reference herein in their entirety. The term "microtextured" and its variants is used herein to include and encompass those surfaces, the topographical surfaces described herein (including the cited/incorporated surface descriptions), and other known nanotextured and microtextured surfaces (such as those known incorporating nanopillars similar to the synthetic surfaces modeled after dragonfly and cicada wings).

A microtextured surface for resisting bioadhesion (including at least resisting spreading colonization of one or more microbes) includes at least one patterned polymer surface, which may include a coating on a substrate and/or which may include integrally formed surface features of a larger structure. The microtextured surface will include a plurality of spaced apart features attached to or projected into a base surface so as to provide at least a first feature spacing distance (the lateral distance between adjacent features). The features each have at least one microscale dimension. As used herein, "microscale" includes micron size or smaller, thus including microscale and nanoscale. At least one neighboring feature will have a substantially different geometry than other neighboring features.

The microtextured surface will provide an average roughness factor (R) of from 2 to 50, preferably being at least 4. The roughness factor (R) is a measure of surface roughness. R is defined herein as the ratio of actual surface area ($R_{act}$) to the geometric surface area ($R_{geo}$); $R=R_{act}/R_{geo}$). For example, if a 1 cm$^2$ piece of material has a completely flat surface, the actual surface area and geometric surface area would both be 1 cm$^2$. However if the flat surface is roughened by patterning, such as using photolithography and selective etching, the resulting actual surface area becomes much greater that the original geometric surface area due to the additional surface area provided by the sidewalls of the features generated (whether they are regularly patterned, irregularly patterned, or unpatterned).

For example, if roughening the exposed surface area doubles the actual surface area of the original flat surface, the R value will be 2. The microtexture generally provides a roughness factor (R) of at least 2. It is believed that the effectiveness of a patterned coating according to the present embodiments will improve with increasing pattern roughness above an R value of about 2, and then likely level off upon reaching some higher value of R. In some preferred embodiments, the roughness factor (R) may be at least 4, such as 5, 6, 7, 8, 9, 10 11, 12, 13, 14, 15, 16, 17, 18, 19, 20, 25 or 30. If the integrity of the catheter wall thickness can be maintained in different embodiments, deeper and more closely spaced features can be provided, such that R values can be higher than 30. In preferred microtextured surfaces, at least two surface feature dimensions each will be less than 50 μm (e.g., height and width, height and length, width and length). In some embodiments, at least two surface feature dimensions may be less than 10 μm, or—in certain preferred embodiments—equal to or less than 2 μm, but still greater than 0.10 μm.

Depending upon the spacing of the microtexturing features, as well as their geometry and composition, the microtextured surface(s) will effectively resist spreading and/or colonization of microbes as compared to the base (non-textured) catheter surface. Microtexture surface features are generally raised surfaces (positive volumes) which emerge from a base level to provide a first feature spacing, or in the case of hierarchical multi-level surface structures according to the present embodiments also include a second feature spacing being the spacing distance between neighboring plateaus (positive volumes), which themselves preferably include raised features thereon. However, as noted above, features can also be projected into a base surface (cavities/negative volumes). In both types of surfaces, there are recesses—expressed as gaps and/or channels between the raised features in the former (plateaus), and expressed as cavities in the latter. If the feature spacing is smaller than the smaller dimension of the organism or cell, it has been found that the microbial adhesion, migration, and/or colony growth is generally retarded, such between 0.25 and the smaller dimension of the cell or organism. A feature spacing of about ½ the smaller dimension of a given organism to be repelled or at least inhibited has been found to be near optimum.

Microtextured catheter surfaces of the present embodiments may include at least one patterned polymer surface including a plurality of features attached to or projected into a base surface layer. Although the surface is generally described herein as being an entirely polymeric construction, the surface (whether integrally part of the catheter wall or configured as a coating) may include non-polymeric elements that can contribute to its viscoelastic and topographical properties. A "feature" as used herein is defined a volume (L, W and H) that projects out from a base plane of the base material or an indented volume (L, W and H) which projects into the base material. The claimed topography for the presently described catheter embodiments is not limited to a specific absolute or relative catheter length. Further, the particular microtexture surface features are not limited to particular lengths, where a feature length (for a catheter) could extend longitudinally, circumferentially, or anywhere in between—except that a longitudinal length preferably would have at least one or more effective terminating gap(s).

For example, an individual surface feature could extend around the entire catheter circumference, separated by a parallel second feature doing the same. For a more hypothetical example, two ridges of an infinite length parallel to one another would define a channel therebetween. In contrast, by reducing the overall lengths of the ridges one can form individual pillars or plateaus. If the microtextured surface is provided as a coating, it may include a different material as compared to the base material of the catheter, but the present disclosure should be read as including embodiments where a coating and base layer may be formed from the same material, or are provided as a monolithic design, either of which can be obtainable by molding, extrusion, or other means. Each of the features will have at least one microscale dimension. In some embodiments, the top surface of at least some of the features are generally, substantially, or exactly flat planar, while others may be contoured, irregular, curved (e.g., to match curvature of a catheter inner and/or outer diameter.

Although feature spacing may be a highly important design parameter, dimensions of individual features can also be significant for preferred functional efficacy. In a certain preferred embodiments of catheter microtextured surfaces, each of the features will include at least one neighboring feature having a "substantially different geometry". Here, the term "substantially different geometry" is defined as providing at least one dimension that is at least 10%, more preferably 50% and most preferably at least 100% larger than a smaller comparative dimension of the feature. The feature length or width is generally used to provide the substantial difference. Regarding the prevention of bioadhesion and/or inhibition of spreading microbe colonization, the width of the features in architectures according to the present embodiments are preferably about 50% to about 75% (and may be 50.0% to 75.0%) of the overall dimensions (length and/or diameter) of a cell or organism attempting to settle, bond, attach, and/or spread on an overall surface, but can—in other embodiments—be larger or smaller than this range. For example, E. coli bacteria are typically about 2 μm long and about 0.5 μm wide (rod-shaped), so that a microtextured surface pattern configured for inhibiting their spread may include feature widths of about 0.25 μm to about 1.5 μm (that is, 50% of 0.5 μm up to about 75% of 2 μm). As another example, S. epidermis and S. aureus bacteria are typically about 0.5 μm to about 1.5 μm in diameter, so that a microtextured surface pattern configured for inhibiting their spread may include feature widths of about 0.25 µm to about 1.125 µm (that is, 50% of 0.5 µm up to about 75% of 2 µm).

Figure 3A:
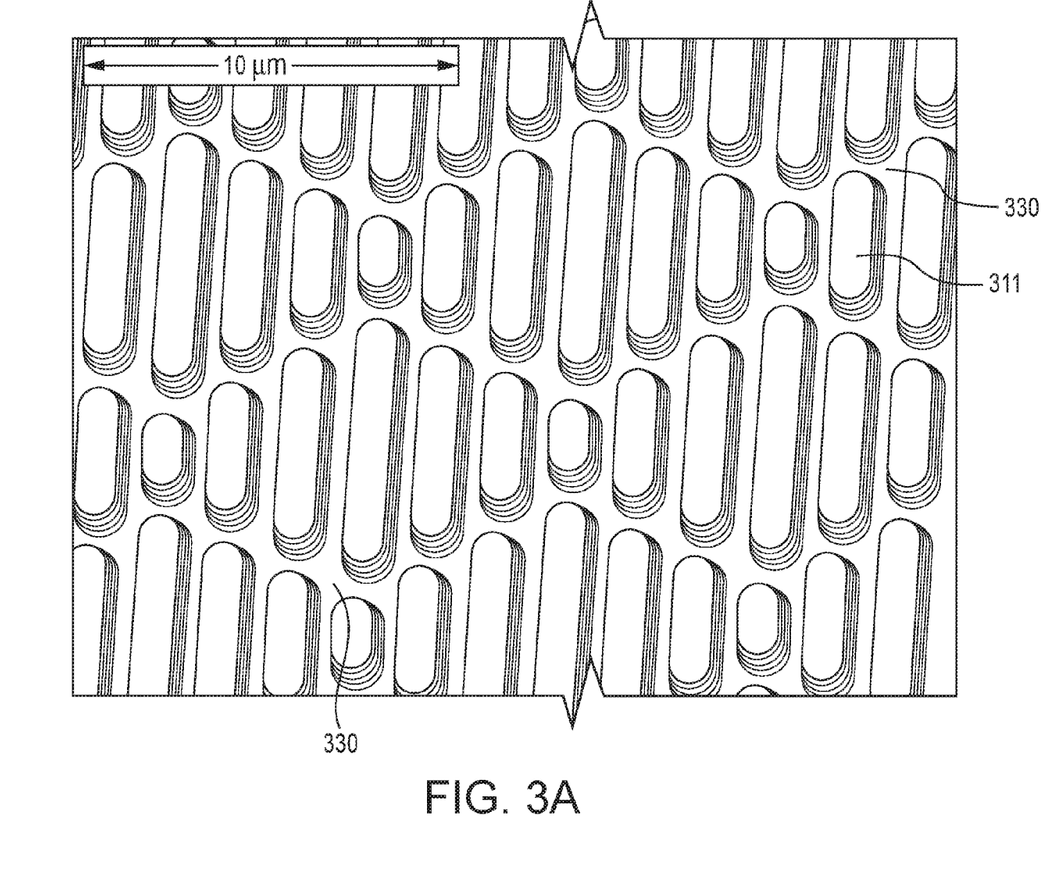
FIGS. 3A-3F show examples of microtexturing patterns that may be used on internal and/or external surfaces of the drainage tube assembly of FIG. 2.

FIG. 3A is a diagrammatic depiction of a scanned SEM image of an exemplary anti-microbial-colonization surface architecture, showing a size/scale bar that is approximate. The microtextured surface (whether embodied as a coating layer or integral with the catheter body) includes a plurality of features 311 that project out from a base surface 330. The base surface 330 can be the inner surface or the outer surface of one of the body drainage catheter embodiments described herein. Each of the features 311 has at least one microscale dimension, with a width of about 1.5 µm, lengths of from about 1.5 to about 8 µm, and a feature spacing of about 0.75 µm. The thickness (height) of feature 311 above the base surface 330 is about 1.5 µm. Features adjacent to a given feature 311 generally provide a variety of substantially different dimensions (e.g., lengths of the features differ, as illustrated). The top surface of the features is shown as being flat planar.

Figure 3B:
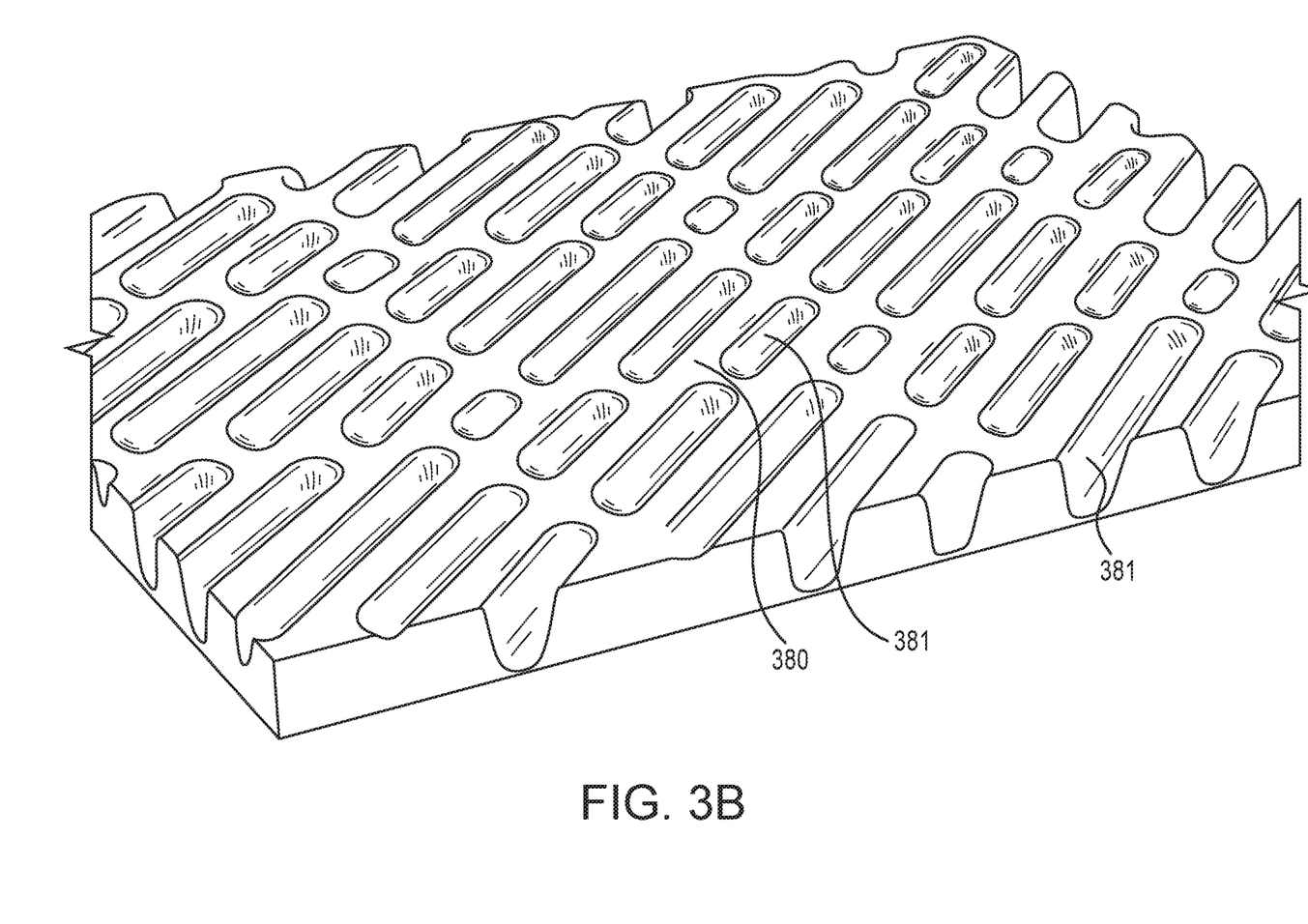

FIG. 3B is a diagrammatic image of a pattern having a plurality of features 381 projecting into a base surface 380, according to another embodiment. Features 381 include indented void volumes into the base surface 380. Although not shown, it should be appreciated that, in certain embodiments, the base surface can also include regions having raised features (e.g., like features 311 shown in FIG. 3A).

Figure 4:
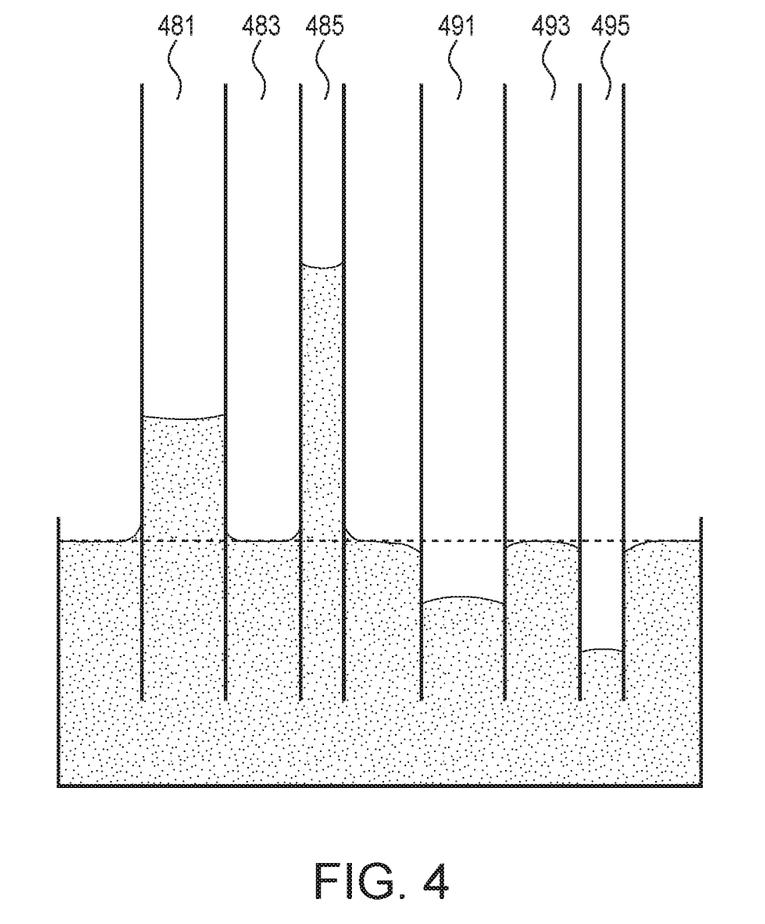
FIG. 4 shows a diagrammatic depiction of surface tension interactions between liquids and walls of channels/recesses.

When applied to a base catheter construction of a different compound, the composition of the patterned coating layer may include or be composed of a polymethylsiloxane (PDMS) elastomer (e.g., SILASIC T2™ available from Dow Corning Corp). In certain embodiments, the base material may be a polymer of the types typically used in patient body drainage catheters (e.g., silicone, various polyether block amides, nylon, and/or other compounds known in the broad catheter art). Other coating and/or catheter construction materials may include a polymer, such as an elastomer of a relative low elastic modulus. The features 311/381 do not need to be formed from a single polymer. Features can be formed from copolymers, polymer composites, steel, aluminum, ceramic, or other materials. The surface layer preferably will be hydrophobic, but can also be neutral or hydrophilic. Hydrophobicity and hydrophilicity are relative terms. A simple, quantitative method for defining the relative degree of interaction of a liquid with a solid surface is the contact angle of a liquid droplet on a solid substrate. When the contact angle of water is less than 30°, the surface is designated hydrophilic because the forces of interaction between water and the surface nearly equal the cohesive forces of bulk water, and water does not cleanly drain from the surface. If water spreads over a surface, and the contact angle at the spreading front edge of the water is less than 10° (high degree of wetting), the surface is often designated as superhydrophilic provided that the surface is not absorbing the water, dissolving in the water or reacting with the water. On a hydrophobic surface, water forms distinct droplets. As the hydrophobicity increases, the contact angle of the droplets with the surface increases. Surfaces with contact angles greater than 90° are designated as hydrophobic, where this surface property is illustrated in FIG. 4 and discussed below with reference thereto.

As noted above, the microtextured surface may also provide surface elastic properties which can influence the degree of bioadhesion and/or microbe colonization directly, and in some cases, may also modulate surface chemistry of the coating layer. It is believed that a low elastic modulus of the patterned coating layer tends to retard bioadhesion, while a high elastic modulus tends to promote bioadhesion. A low elastic modulus is generally from about 10 kPa and 10 MPa, while a high elastic modulus is generally at least 1 GPa.

Figure 3C:
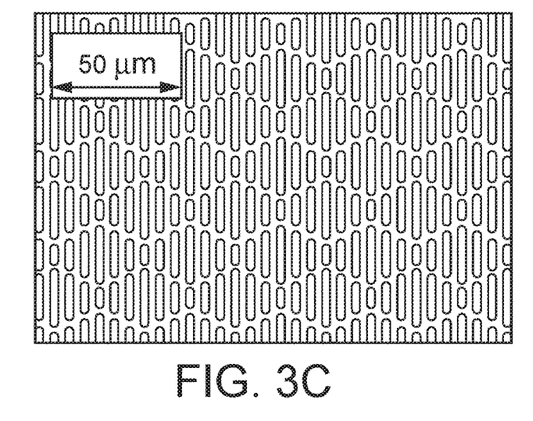
Figure 3D:
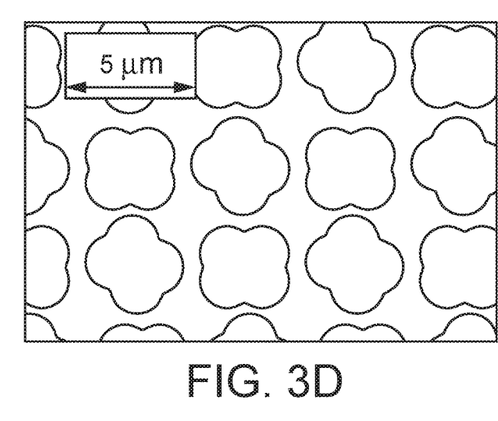
Figure 3E:
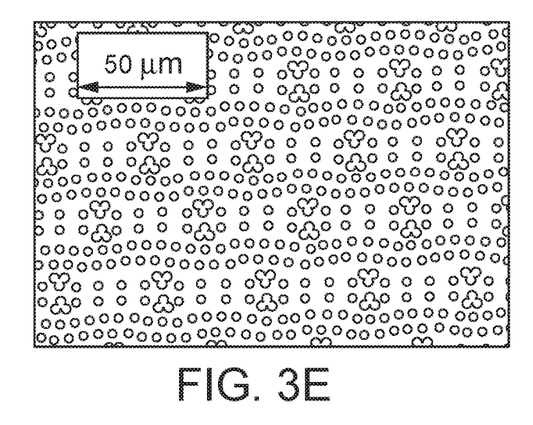
Figure 3F:
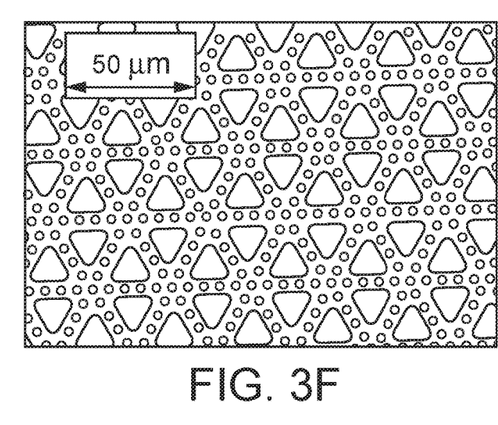

FIGS. 3C-3F illustrate some other examples of architectural or topographical patterns (unit cells) that can be used with microtextured surface regions of presently-disclosed catheter embodiments. FIG. 3C shows a riblet pattern, which may be fabricated from PDMS elastomer having features spaced about 2 µm apart, although illustrated at a somewhat different scale in FIG. 3C. The features were formed thereon (and/or on other surfaces discussed herein) may be formed using conventional photolithographic processing, or other methods known in the art. FIG. 3D shows a star/clover pattern, FIG. 3E a gradient pattern, while FIG. 3F shows a triangle/circle pattern. Examples of dimensions/scales are shown in the drawings, but it should be appreciated that those numbers are illustrative only, and the exact dimensions of surface features in these various microtexturing patterns can be varied to suit particular catheter sizes and/or particular microbes being targeted for inhibition. Those of skill in the art will appreciate that the illustrated patterns are not the only microtextured surfaces that will provide the advantageous features contemplated herein. As such the present disclosure and claims should also be understood to encompass internal and external catheter surfaces that include microtextured surfaces including circumferential parallel rings and or intersecting rings (where a plurality micropatterned grooves and/or upstanding features relative to a base surface each extend around an entire circumferential outer diameter surface, inner diameter surface, or both, where size of—and the spacing between—adjacent surface features is configured to inhibit colonization and or other growth of microbes based upon the relative and absolute size of those surface features including the spaces therebetween.

Typically and historically, the surfaces of drainage catheters have been kept as smooth as possible upon the conventional belief that such surfaces will be easier to clean and keep clean without harboring microbes that could colonize/expand and cause harm or at least inconvenience to a patient. The presently described embodiments differ from that prior pattern. Also, it is contemplated within the present disclosure that the microtextured surfaces described herein may provide extended benefits by treatment with antimicrobial agents (as compared to untreated microtextured surfaces, treated non-microtextured surfaces, and treated non-microtextured surfaces).

Antimicrobial agents in the form of (and/or carried by) a liquid can provide a coating/residue on a microtextured surface, including being retained in liquid form having volume within negative-volume cavities and between positive-volume features of a microtextured surface. Liquid formulations suitable for this purpose will have a surface tension that allows the liquid to penetrate and be held at least partially on or within the cavities, channels, wells, and/or other portions (below an upper plane, whether for raised or recessed features). Subject to variations in the surface energy properties of the catheter surface materials, lower surface tension liquids will tend to coat/cover all surfaces of microtextured surface features.

Surface tension is a contractive tendency of the surface of a liquid that allows it to resist an external force. Surface tension is an important property that markedly influences the ecosystem. The net effect is an inward force at its surface that causes water to behave as if its surface were covered with a stretched elastic membrane. Because of the relatively high attraction of water molecules for each other, water has a high surface tension (72.8 millinewtons per meter at 20° C.) compared to that of most other liquids. The cohesive forces between liquid molecules are responsible for the phenomenon known as surface tension. The molecules at the surface do not have other like molecules on all sides of them and consequently they cohere more strongly to those directly associated with them on the surface. This forms a surface "film" which makes it more difficult to move an object through the surface than to move it when it is completely submersed.

Surface tension is typically measured in dynes/cm, the force in dynes required to break a film of length 1 cm. Equivalently, it can be stated as surface energy in ergs per square centimeter. Water at 20° C. has a surface tension of 72.8 dynes/cm compared to 22.3 for ethyl alcohol and 465 for mercury. Diagrammatic illustration is shown in FIG. 4 of capillary rise and fall due to surface tension. The leftmost four taller liquid-contacting walls (defining three vertical channels 481, 483, 485) are hydrophilic, and the liquid/solid contact angle is less than 90°. The rightmost four taller liquid-contacting walls (defining three vertical channels 491, 493, 495) are hydrophobic, and the liquid/solid contact angle is greater than 90°, each relative to a horizontal transect of the channel, where the corresponding channels (4×1, 4×3, 4×5) have the same inner diameters so that the only difference between each pair is the hydrophilicity/hydrophobicity of the surface. If a tube is sufficiently narrow and the liquid adhesion to its walls is sufficiently strong, surface tension can draw liquid up the tube in a phenomenon known as capillary action (e.g., channels 481, 485). This means the size and the material characteristics of the microtextured surface pattern features are important, as is the formulation into which the antimicrobial or repellent compound is solubilized, because the capillary action or lack thereof ultimately relies upon the difference/balance between respective surface energies of the liquid and the solid that the liquid contacts.

For example, surface texturing/channeling on the outer diameter surface and/or inner diameter surface of catheter tubing may be treated with a solution that includes 2% chlorhexidine gluconate (CHG) and 70% isopropyl alcohol (IPA). This formulation is known to destroy virtually all contacted microbes and can stay within the channels (e.g., intra-feature grooves/spaces) for a long period of time, where at least the CHG molecules can chemically enhance the topographical resistance to/inhibition of microbial colonization and migration across the microtextured surface. In particular, the CHG molecules can stay within the channels where they are protected from being wiped away during regular preparation steps of the drainage catheter (during which the surface is washed with a CHG solution and/or scrubbed with a CHG-solution infused wiping cloth/"wipe," then wiped off with a clean dry gauze or other material). This application preferably will be for those proximal portions of catheters that are external to the patient. The ability to enhance inhibition of bacterial growth by chemical means from within the channels provides further advantage over known/prior microtextured topographical surfaces. In addition, each time these catheters are cleaned (e.g., with the solution noted above or any other solution with at least one component having a molecular size and stability to reside in the inner-feature channels, those channels can be replenished to support their antimicrobial benefit. A carrier material such as a gel, paste, non-volatile liquid, or other material (including at least one antimicrobial agent)—most preferably with surface tension and physical properties that will enhance retention within the inter-feature channels (and/or cavities) of microtextured surfaces—will provide additional benefit in inhibiting (that is reducing likelihood) of microbial colonization and/or migration toward a patient along a catheter surface. Most preferably the active agent (whether CHG or other) and the carrier material (if present) will not impair the topographical function of a treated microtextured surface by "clogging" the gaps and/or otherwise providing a path for microbes across/between different microtextured surface features.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Specifically, each of the microtexturing patterns illustrated and those textually described may be used on one or more inner and/or outer surface(s) of a body drainage catheter, and those patterns may be combined with each other in the same, adjacent, or separate/different locations within a single body cavity drainage catheter device. Although specific terms are employed herein, they are used in a generic and descriptive sense only and not for purposes of limitation unless specifically defined by context, usage, or other explicit designation.

It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

We claim:

1. A body cavity drainage catheter, comprising:
  an elongate tubular body including a longitudinal lumen defined by a catheter wall;
  a first lengthwise portion of the tubular body configured for indwelling a patient body;
  a second lengthwise portion of the tubular body configured for disposition outside a patient body and further including a valve at a terminal end of the tubular body;
  a cuff element defining a border between the first lengthwise portion and the second lengthwise portion, said cuff configured for ingrowth by patient tissue in a manner forming an effective seal around an outer diameter of the tubular body;
  at least one lengthwise region of the second lengthwise portion including a microtextured surface disposed along an inner diameter surface, an outer diameter surface, or both; and
  at least one antimicrobial compound disposed within recesses of the microtextured surface;
  wherein the recesses each include at least one dimension of less than 50 μm; and
  wherein the at least one dimension of the recesses and a surface tension of a liquid comprising the antimicrobial compound are selected such that the liquid is drawn into the recesses and is held within the recesses by capillary action at 20° C.

2. The catheter of claim 1, further including a plurality of fenestrations through the catheter wall providing a path of fluid communication to/from the lumen, and where the microtextured surface is effective to inhibit colonization and/or migration of microbes on said surface.

3. The catheter of claim 1, where the at least one lengthwise region of the second lengthwise portion including a microtextured surface is disposed immediately adjacent the valve.

4. The catheter of claim 1, where the at least one lengthwise region of the second lengthwise portion including a microtextured surface is disposed immediately adjacent the cuff.

5. The catheter of claim 1, where the at least one lengthwise region of the second lengthwise portion including a microtextured surface includes a plurality of lengthwise regions.

6. The catheter of claim 1, where the antimicrobial compound comprises chlorhexidine gluconate.

7. The catheter of claim 1, where the antimicrobial compound is comprised by a carrier material.

8. The catheter of claim 7, where the carrier material comprises an alcohol.

9. The catheter of claim 1, comprising a plurality of microtextured surface features dimensioned to include at least two surface dimensions of less than 50 µm.

10. The catheter of claim 1, comprising a plurality of microtextured surface features dimensioned to include at least two surface dimensions of less than 10 µm.

11. The catheter of claim 1, comprising a plurality of microtextured surface features dimensioned to include at least two surface dimensions of less than 2 µm.

12. A body cavity drainage catheter, comprising:
an elongate tubular wall radially surrounding a longitudinal catheter lumen;
a distal lengthwise portion of the elongate tubular wall including a plurality of fenestrations through the wall providing a path of fluid communication to/from the catheter lumen;
a proximal lengthwise portion of the elongate tubular wall including a valve at a proximal terminal end of the tubular wall;
a cuff element surrounding and defining a border between the proximal lengthwise portion and the distal lengthwise portion, said cuff configured for ingrowth by patient tissue in a manner forming an effective seal around an outer diameter of the tubular wall; and
at least one lengthwise region of the proximal lengthwise portion including at least one microtextured surface disposed along an inner diameter surface, an outer diameter surface, or both where the microtextured surface includes a plurality of surface features dimensioned to include at least two surface dimensions of less than 50 µm;
wherein at least one space between adjacent surface features contains at least one antimicrobial agent;
wherein the at least one space between adjacent surface features includes at least one dimension of less than 50 µm; and
wherein the at least one dimension of the at least one space and a surface tension of a liquid comprising the antimicrobial compound are selected such that the liquid is drawn into the at least one space and is held within the at least one space by capillary action at 20° C.

13. The catheter of claim 12, where the antimicrobial agent comprises chlorhexidine gluconate.

14. The catheter of claim 12, where the antimicrobial agent is comprised by a carrier material.

* * * * *